United States Patent
Marciniec et al.

(10) Patent No.: US 9,018,400 B2
(45) Date of Patent: Apr. 28, 2015

(54) FUNCTIONALIZED POLYHEDRAL OCTAVINYLSILSESQUIOXANES AND A METHOD TO OBTAIN THE FUNCTIONALIZED POLYHEDRAL OCTAVINYLSILSESQUIOXANES

(75) Inventors: Bogdan Marciniec, Swarzedz (PL); Cezary Pietraszuk, Wroclaw (PL); Mariusz Majchrzak, Poznan (PL); Patrycja Zak, Poznan (PL)

(73) Assignee: Adam Mickiewicz University, Poznañ (PL)

( * ) Notice: Subject to any disclaimer, the term of this patent is extended or adjusted under 35 U.S.C. 154(b) by 0 days.

(21) Appl. No.: 13/807,125

(22) PCT Filed: Aug. 4, 2011

(86) PCT No.: PCT/PL2011/000084
§ 371 (c)(1),
(2), (4) Date: Dec. 27, 2012

(87) PCT Pub. No.: WO2012/023867
PCT Pub. Date: Feb. 23, 2012

(65) Prior Publication Data
US 2013/0102793 A1    Apr. 25, 2013

(30) Foreign Application Priority Data
Aug. 20, 2010  (PL) .......................... 392166

(51) Int. Cl.
C07F 7/21    (2006.01)
(52) U.S. Cl.
CPC ....................... C07F 7/21 (2013.01)
(58) Field of Classification Search
USPC .............................. 549/4; 556/461
See application file for complete search history.

(56) References Cited

PUBLICATIONS

Patrycja Zak et al., Highly effective synthesis of vinylfunctionalised cubic silsesquioxanes, 2011, Journal of Organometallic Chemistry, 696, 887-891.*
Feher et al., "Cross-metathesis of alkenes with vinyl-substituted silsesquioxanes and spherosilicates: a new method for synthesizing highly-functionalized Si/O frameworks," Chem. Commun., 1997, pp. 1185-1186.
Itami et al., "Functionalization of Octavinylsilsesquioxane by Ruthenium-Catalyzed Silylative Coupling versus Cross-Metathesis," Chem. Eur. J. , 2004, pp. 1239-1248, vol. 10, published by Wiley-VCH Verlag GmbH & Co. KGzA.
Sellinger et al., "Heck coupling of haloaromatics with octavinylsilsesquioxane: solution processable nanocomposites for application in electroluminescent devices," Chem. Commun., 2005, pp. 3700-3702.
Kawakami et al., "Hydrogen-Bonding 3D Networks by Polyhedral Organosilanols: Selective Inclusion of Hydrocarbons in Open Frameworks," Organometallics, 2010, pp. 3281-3288, vol. 29.
Sulaiman et al., "Molecules with Perfect Cubic Symmetry as Nanobuilding Blocks for 3-D Assemblies. Elaboration of Octavinylsilsesquioxane. Unusual Luminescence Shifts May Indicate Extended Conjugation Involving the Silsesquioxane Core," Chemistry of Materials, 2008, pp. 5563-5573, vol. 20.
Lo et al., "Organic-Inorganic Hybrids Based on Pyrene Functionalized Octavinylsilsesquioxane Cores for Application in OLEDs," Journal of the American Chemical Society, 2007, pp. 5808-5809, vol. 129.
Lo et al., "Silsesquioxane-Based Nanocomposite Dendrimers With Photo-luminescent and Charge Transport Properties," The Chemical Record, 2006, pp. 157-168, vol. 6, published by The Japan Chemical Journal Forum and Wiley Periodicals, Inc.
International Search Report issued in International Patent Application No. PCT/PL2011/000084 dated Oct. 28, 2011.

* cited by examiner

Primary Examiner — Kristin Vajda
(74) Attorney, Agent, or Firm — Oliff PLC

(57) ABSTRACT

A new functionalized polyhedral octavinylsilsesquioxanes having the general formula 1, in which $R^1$ denotes: (1) any aryl group other than a non-substituted phenyl or a phenyl substituted in position four with a halogen or the groups-trimethylsilylethynyl, 4,4,5,5-tetramethyl-1,3-dioxaborolane-2-yl, 3,4-dimethoxyphenyl, 3',5'-bis(methoxycarbonyl) phenyl or benzo[d][1,3]-dioxol-5-yl; (2) any heteroaryl group; or (3) groups including coupled aromatic rings. Additionally, a method to obtain new and known functionalized polyhedral octavinylsilsesquioxanes having the general formula 1, by the silylating coupling of octavinylsilsesquioxane with olefins in the presence of a ruthenium complex catalyst.

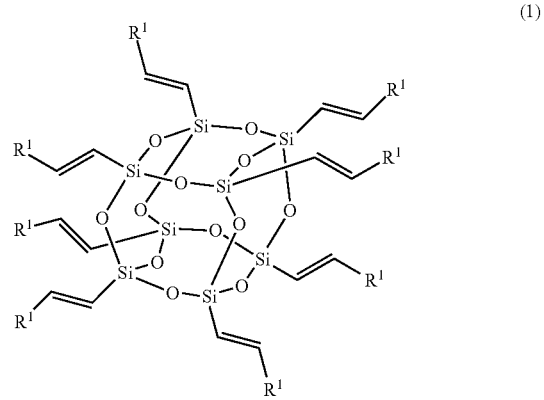

(1)

1 Claim, No Drawings

FUNCTIONALIZED POLYHEDRAL OCTAVINYLSILSESQUIOXANES AND A METHOD TO OBTAIN THE FUNCTIONALIZED POLYHEDRAL OCTAVINYLSILSESQUIOXANES

This invention relates to new functionalized polyhedral octavinylsilsesquioxanes and a method to obtain the new and known functionalized polyhedral octavinylsilsesquioxanes.

Functionalized polyhedral octavinylsilsesquioxanes containing an inorganic siloxane skeleton connected with a wide range of functional groups are a convenient starting material for obtaining hybrid materials and are applicable as nano-fillers in new-generation composite materials.

Feher (1) described functionalization by means of a cross-metathesis reaction catalyzed by molybdenum complexes. Catalysts used in the method are hard to synthesize and sensitive to moisture and atmospheric oxygen, which considerably limits its application.

The cross-metathesis reaction (2) with the use of ruthenium complexes is very efficient and selective, although the presence of certain types of functionalized olefins prevents its use because of deactivation of the catalyst taking place, therefore, it cannot be used at all times.

Sellinger (3) described the functionalization of octavinylsilsesquioxanes by means of the Heck coupling reaction catalyzed with palladium complexes, but the reaction is not stereo- or chemoselective.

Disclosed in the Patent Application No. P-389429 is a method for the synthesis of functionalized monovinylsilsesquioxanes by means of a silylating coupling reaction.

It is an objective of the invention to provide new functionalized polyhedral octavinylsilsesquioxanes and a method to obtain the new and known functionalized polyhedral octavinylsilsesquioxanes.

This invention relates to new functionalized polyhedral octavinylsilsesquioxanes having the general formula 1, in which:

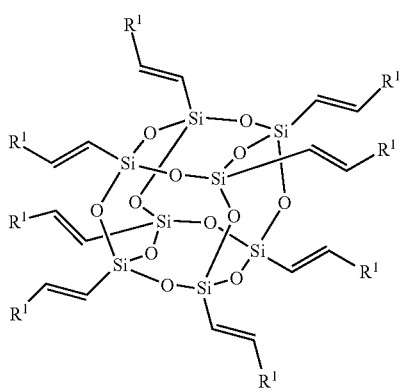

(1)

$R^1$ denotes:
any aryl group other than a non-substituted phenyl or a phenyl substituted in position four with a halogen or the groups: trimethylsilylethynyl, 4,4,5,5-tetramethyl-1,3-dioxaborolane-2-yl, 3,4-dimethoxyphenyl, 3',5'-bis(methoxycarbonyl)phenyl or benzo[d][1,3]-dioxol-5-yl,
any heteroaryl group,
groups comprising coupled aromatic rings.

Another aspect of the invention relates to a method to obtain new and known functionalized polyhedral octavinylsilsesquioxanes having the general formula 1, in which:

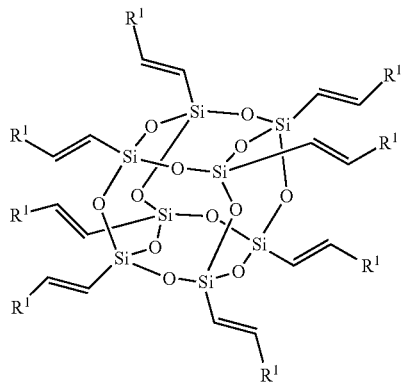

(1)

$R^1$ denotes:
any aryl or hetero aryl group; groups comprising coupled aromatic rings,
any aryl or heteroaryl group substituted with equal or different substituents selected from the group: alkyl, alkenyl, alkynyl, aryl, alkoxyl, aryloxyl, halogen and substituents comprising heteroatoms selected from the group: N, O, P, S, Si, B,
$CF_3$ group,
a group having the general formula 2:

—O—$R^2$  (2)

in which $R^2$ denotes:
an aliphatic group $(CH_2)_nCH_3$, in which n=0-25, any aryl or hetero aryl group, including substituted aryl or hetero aryl groups;
substituents containing heteroatoms selected from the group comprising: N, O, P, S, Si, B
by the silylating coupling of octavinylsilsesquioxane having the general formula 3,

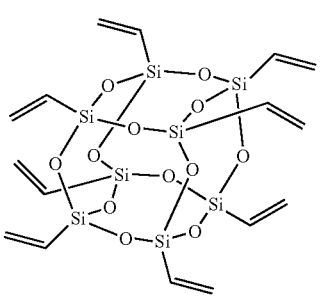

(3)

with olefins having the general formula 4,

(4)

in which $R^1$ is specified above, in the presence of a ruthenium complex catalyst.

The catalyst is usually a compound having the general formula 5

in which $R^4$ denotes:
for n=3 denotes triphenylphosphine,
for n=2 denotes tricyclohexylphosphine or triisopropylphosphine.

The catalyst is used in an amount from $1\times10^{-3}$ to $1\times10^{-1}$ mole of Ru per 1 mole of vinyl groups in silsesquioxane, preferably from $0.5\times10^{-2}$ to $2\times10^{-2}$ and most preferably $1\times10^{-2}$ mole.

Addition of a copper salt as co-catalyst (specifically copper (I) salt, most preferably copper(I) chloride) in the amount of $10^{-1}$–10 moles of Cu (preferably 5 moles of Cu) per mole of Ru, has a favourable effect on the reaction course.

The reaction is carried out in a solvent under inert gas in an open or closed system and, preferably, the gas is used after any oxygen or moisture has been removed therefrom. In open systems, the reaction is carried out at temperatures not higher than the reaction mixture boiling point. In closed systems, the reactions are carried out at temperatures not higher than 200° C. Preferably, though not necessarily, an excess of olefin relative to the octavinylsilsesquioxane is used, to speed up the reaction. Preferably, the olefin is used in an excess of from 1.1 to 2, most preferably approximately 1.5, moles of olefin per mole of $CH_2$=CH groups in octavinylsilsesquioxane.

The reaction is carried out in solvents selected from the group comprising: aromatic organic compounds, chlorinated aliphatic compounds, chlorinated aromatic compounds. The reaction is preferably carried out in methylene chloride or toluene.

In the method of the invention, the reactor is filled under inert gas with a suitable amount of octavinylsilsesquioxane, solvent, and alkene and catalyst and, optionally, co-catalyst, upon which the reaction mixture is stirred and heated, preferably, to a temperature which is optimum for the given system of reagents and solvent. The reaction is continued for 1-48 hours at a temperature in the range 20-200° C., preferably, at a temperature in the boiling range of the reaction mixture. The catalyst is preferably added after mixing and heating the other reactants. The co-catalyst is preferably added after the catalyst.

Preferably, all the reagents are dewatered and deoxidized prior to being reacted.

In the case of reactions effected in closed systems, the reaction is carried out in the same conditions as in open systems, using higher temperatures for 1-48 hours at temperatures up to 200° C. A raw product is separated from the reaction mixture by precipitation using an appropriate solvent, in which the product will not get dissolved, or by removing the solvent in which the reaction was effected. In the latter case, after evaporating the solvent, the catalyst is removed by eluting with a solvent which dissolves selectively the catalyst alone. Preferably, hexane is used for precipitating the product or eluting the catalyst. A raw product is further purified by known methods, depending on its intended use.

Application, in the method of the invention, of the silylating coupling process enables the synthesis of functionalized polyhedral silsesquioxanes with high yields and selectivities.

Modification of polyhedral vinylsilsesquioxanes with suitably designed groups—chromophores with π-coupled systems—enables [them] to be used, for instance, in electrochemistry for polymerization or as materials with controlled fluorescence and photoluminescence, characterized by specific photophysicochemical parameters.

The method of the invention shall now be illustrated by way of Examples which are not intended to limit the scope of applicability of the invention.

The product analysis is performed as follows:
$^1$H and $^{13}$C-NMR spectra were obtained using the spectrometer Varian Gemini 300, at 300 and 75 MHz
$^{29}$Si spectra were obtained using the spectrometer Varian Avance 600, at 119, 203 MHz. All NMR measurements were performed after filling the test tubes under argon. Deoxidized and dewatered, deuterated benzene was used as solvent. The measurements were performed at a room temperature.
mass spectra: were obtained using 4000 Q TRAP from Applied Biosystems,

EXAMPLE I

A 5 mL reactor, equipped with a magnetic stirrer, a reflux condenser with an attachment enabling the reaction system to be connected to a vacuum-and-gas line was filled under inert gas with 0.01 g ($1.58\times10^{-5}$ mol) octavinylsilsesquioxane, followed, in the following order, with 3 mL methylene chloride and 0.019 mL ($1.26\times10^{-4}$ mol) 4-(trifluoromethyl)styrene. The reaction mixture was warmed to 45° C. while stirring continuously. Then 0.0009 g ($1.26\times10^{-6}$ mol) [chlorohydridocarbonylbis(tricycle-hexylphosphine)ruthenium(II)] was added to the mixture and 5 minutes later 0.0006 g ($6.32\times10^{-6}$ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:$CH_2Cl_2$=10:1 and transferred to a silica-packed chromatographic column to purify the product. This produced octakis[2-(4-trifluoromethylphenyl)ethenyl]octasilsesquioxane in the form of white powder with a yield of 90%. Melting range: 320-324° C.

$^1$H NMR ($C_6D_6$, ppm): δ=6.58 (d, 8H, J=19.3 Hz, =CHSi), 7.08 (d, 16H, J=8.5 Hz, $C_6H_4$—$CF_3$), 7.22 (d, 16H, J=8.5 Hz, $C_6H_4$—$CF_3$), 7.61 (d, 8H, J=19.3 Hz, =CH—Ar)

$^{13}$C NMR ($C_6D_6$, ppm): δ=119.9 (=CHSi), 126.0 (q, $CF_3$), 127.4, 128.1 ($\underline{C}_6H_4$—$CF_3$), 131.4 (q, ipso-C at $CF_3$), 140.1 (ipso-C at $C_6H_4$-$CF_3$), 149.2 (=CHAr)

$^{29}$Si NMR ($C_6D_6$, ppm): δ=−78.32

APPI-MS: m/z ([M+H]$^+$, % intensity): 1777 (76), 1778 (100), 1781 (54), 1782 (78), 1784 (54), 1786 (41), 1787 (29)

EXAMPLE II

A 5 mL reactor, equipped with a magnetic stirrer, a reflux condenser with an attachment enabling the reaction system to be connected to a vacuum-and-gas line was filled under inert gas with 0.01 g ($1.58\times10^{-5}$ mol) octavinylsilsesquioxane, followed, in the following order, with 3 mL methylene chloride and 0.035 g ($1.26\times10^{-4}$ mol) 4-(9-anthraceneyl)styrene. The reaction mixture was warmed to 45° C. while stirring continuously. Then 0.0009 g ($1.26\times10^{-6}$ mol) [chlorohydridocarbonylbis(tricycle-hexylphosphine)ruthenium(II)] was added to the mixture and 5 minutes later 0.0006 g ($6.32\times10^{-6}$ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:$CH_2Cl_2$=10:1 and transferred to a silica-packed chromatographic column to purify the product. This produced octakis[2-{4-(9-anthracenyl)

phenyl}ethenyl]octasilsesquioxane in the form of a yellow crystalline solid with a yield of 83%. Melting range: 294-298° C.

$^1$H NMR (C$_6$D$_6$, ppm): δ=6.93 (d, 8H, J=19.0 Hz, =CHSi), 7.11-7.28 (m, 32H, anthracene), 7.26 (d, 16H, J=8.2 Hz, —C$_6$H$_4$—), 7.56 (d, 16H, J=8.2 Hz, —C$_6$H$_4$—), 7.79 (d, 16H, J=8.5 Hz, anthracene), 7.85 (d, 16H, J=8.0 Hz, anthracene), 8.09 (d, 8H, J=19.0 Hz, =CH—Ar), 8.25 (s, 8H, anthracene)

$^{13}$C NMR (C$_6$D$_6$, ppm): δ=118.3, 125.4, 125.8, 127.2, 127.3, 127.6, 127.7, 128.7, 130.7, 131.9, 132.0, 136.9, 140.1, 150.2

$^{29}$Si NMR (C$_6$D$_6$, ppm): δ=−77.99

EXAMPLE III

A 5 mL reactor, equipped with a magnetic stirrer, a reflux condenser with an attachment enabling the reaction system to be connected to a vacuum-and-gas line was filled under inert gas with 0.01 g (1.58×10$^{-5}$ mol) octavinylsilsesquioxane, followed, in the following order, with 3 mL methylene chloride and 0.029 g (1.26×10$^{-4}$ mol) 4-(1-naphthyl)styrene. The reaction mixture was warmed to 45° C. while stirring continuously. Then 0.0009 g (1.26×10$^{-6}$ mol) [chlorohydridocarbonylbis(triciclehexyl-phosphine)ruthenium(II)] was added to the mixture and 5 minutes later 0.0006 g (6.32×10$^{-6}$ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:CH$_2$Cl$_2$=10:1 and transferred to a silica-packed chromatographic column to purify the product. This produced octakis[2-{4-(1-naphthyl)phenyl}ethenyl]octasilsesquioxane in the form of opalescent solid with a yield of 93%. Melting range: 318-320° C.

$^1$H NMR (400 MHz, CDCl$_3$): δ=6.54 (d, 8H, J=19.5 Hz, =CHSi), 7.39-7.56 (m, 48H, C$_6$H$_4$—C$_{10}$H$_7$), 7.61 (d, 8H, J=19.2 Hz, =CH—C$_6$H$_4$—C$_{10}$H$_7$), 7.72 (d, 16H, J=13.2, 8.1 Hz, —C$_6$H$_4$—C$_{10}$H$_7$), 7.85-7.95 (m, 16H, =CH—C$_6$H$_4$—C$_{10}$H$_7$).

$^{13}$C NMR (75 MHz, CDCl$_3$): δ=117.5 (=CHSi), 125.9, 125.2, 125.6, 125.8, 126.7, 126.8, 127.6, 128.1, 130.2, 131.3, 133.6, 136.3, 139.5, 141.4, 148.6 (=CH—C$_6$H$_4$—Ph).

$^{29}$Si NMR (79 MHz, CDCl$_3$): δ=−77.89.

EXAMPLE IV

A 5 mL reactor, equipped with a magnetic stirrer, a reflux condenser with an attachment enabling the reaction system to be connected to a vacuum-and-gas line was filled under inert gas with 0.01 g (1.58×10$^{-5}$ mol) octavinylsilsesquioxane, followed, in the following order, with 3 mL methylene chloride and 0.029 g (1.26×10$^{-4}$ mol) 4-(1-naphthyl)styrene. The reaction mixture was warmed to 110° C. while stirring continuously. Then 0.0009 g (1.26×10$^{-6}$ mol) [chlorohydridocarbonylbis(tricyclohexyl-phosphine)ruthenium(II)] was added to the mixture. The reaction mixture was heated for 24 hours at a temperature of 110° C. Then the solvent was subjected to vacuum evaporation and the residue was dissolved in a mixture of hexane and methylene chloride at a ratio by volume of hexane:CH$_2$Cl$_2$=10:1 and transferred to a silica-packed chromatographic column to purify the product. This produced octakis[2-{4-(1-naphthyl)phenyl}ethenyl]octasilsesquioxane in the form of opalescent solid with a yield of 51%. NMR analysis as in Example III.

EXAMPLE V

A 5 mL reactor, equipped with a magnetic stirrer, a reflux condenser with an attachment enabling the reaction system to be connected to a vacuum-and-gas line was filled under inert gas with 0.01 g (1.58×10$^{-5}$ mol) octavinylsilsesquioxane, followed, in the following order, with 3 mL methylene chloride and 0.024 g (1.26×10$^{-4}$ mol) 4-(1-thienyl)styrene. The reaction mixture was warmed to 45° C. while stirring continuously. Then 0.0009 g (1.26×10$^{-6}$ mol) [chlorohydridocarbonylbis(tricyclohexylphosphine)ruthenium(II)] was added to the mixture and 5 minutes later 0.0006 g (6.32×10$^{-6}$ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:CH$_2$Cl$_2$=10:1 and transferred to a silica-packed chromatographic column to purify the product. This produced octakis[2-{4-(1-thienyl)phenyl}ethenyl]octasilsesquioxane in the form of yellowish solid with a yield of 90%. Melting range: 283-285° C.

$^1$H NMR (400 MHz, CDCl$_3$): δ=6.35 (d, 8H, J=19.2 Hz, =CHSi), 7.26 (d, 8H, J=3.9 Hz, —C$_6$H$_4$—C$_4$H$_2$S), 7.32 (d, 8H, J=1.2 Hz, —C$_6$H$_4$—C$_4$H$_2$S), 7.32 (d, 8H, J=8.3 Hz, —C$_6$H$_4$—), 7.38 (d, 8H, J=19.1 Hz, =CH—C$_6$H$_4$—), 7.44-7.50 (m, 16H, —C$_6$H$_4$—C$_4$H$_2$S), 7.62 (d, 16H, J=9.6 Hz, —C$_6$H$_4$—).

$^{13}$C NMR (75 MHz, CDCl$_3$): δ=117.4 (=CHSi), 123.5, 125.3, 126.2, 127.7, 128.3, 135.2, 136.6, 144.1, 148.7 (=CH—C$_6$H$_4$—Ph).

$^{29}$Si NMR (79 MHz, CDCl$_3$): δ=−78.20.

EXAMPLE VI

A 5 mL reactor, equipped with a magnetic stirrer, a reflux condenser with an attachment enabling the reaction system to be connected to a vacuum-and-gas line was filled under inert gas with 0.01 g (1.58×10$^{-5}$ mol) octavinylsilsesquioxane, followed, in the following order, with 3 mL methylene chloride and 0.016 mL (1.26×10$^{-4}$ mol) 4-bromostyrene. The reaction mixture was warmed to 45° C. while stirring continuously. Then 0.0009 g (1.26×10$^{-6}$ mol) [chlorohydridocarbonylbis(tricyclohexyl-phosphine)ruthenium(II)] was added to the mixture and 5 minutes later 0.0006 g (6.32×10$^{-6}$ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:CH$_2$Cl$_2$=10:1 and transferred to a silica-packed chromatographic column to purify the product. This produced octakis[2-(4-bromophenyl)ethenyl]octasilsesquioxane in the form of white powder with a yield of 92%. Melting range: 327-330° C.

$^1$H NMR (C$_6$D$_6$, ppm): δ=6.44 (d, 8H, J=19.3 Hz, =CHSi), 6.88 (d, 16H, J=8.5 Hz, C$_6$H$_4$—Br), 7.12 (d, 16H, J=8.5 Hz, C$_6$H$_4$—Br), 7.50 (d, 8H, J=19.3 Hz, =CH—Ar)

$^{13}$C NMR (C$_6$D$_6$, ppm): δ=117.7 (=CHSi), 123.5 (ipso-C at Br of C$_6$H$_4$Br), 128.4 (o-C of C$_6$H$_4$Br), 131.9 (m-C of C$_6$H$_4$Br), 135.7 (ipso-C of C$_6$H$_4$Br), 148.9 (=CHAr)

$^{29}$Si NMR (C$_6$D$_6$, ppm): δ=−78.07

APPI-MS: m/z ([M+H]$^+$, % intensity): 1862 (16), 1867 (19), 1869 (39), 1872 (87), 1873 (90), 1874 (100), 1876 (77), 1877 (52), 1879 (23).

EXAMPLE VII

A 5 mL reactor, equipped with a magnetic stirrer, a reflux condenser with an attachment enabling the reaction system to be connected to a vacuum-and-gas line was filled under inert gas with 0.01 g (1.58×10$^{-5}$ mol) octavinylsilsesquioxane, followed, in the following order, with 3 mL toluene and 0.016 mL (1.26×10⁻⁴ mol) 4-bromostyrene. The reaction mixture was warmed to 45° C. while stirring continuously. Then 0.0009 g (1.26×10⁻⁶ mol) [chlorohydridocarbonylbis(tricyclohexylphosphine)ruthenium(II)] was added to the mixture and 5 minutes later 0.0006 g (6.32×10⁻⁶ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:$CH_2Cl_2$=10:1 and transferred to a silica-packed chromatographic column to purify the product. This produced octakis[2-(4-bromophenyl)ethenyl]octasilsesquioxane in the form of white powder with a yield of 90%.

EXAMPLE VIII

A 5 mL reactor, equipped with a magnetic stirrer, a reflux condenser with an attachment enabling the reaction system to be connected to a vacuum-and-gas line was filled under inert gas with 0.01 g (1.58×10⁻⁵ mol) octavinylsilsesquioxane, followed, in the following order, with 3 mL chlorobenzene and 0.016 mL (1.26×10⁻⁴ mol) 4-bromostyrene. The reaction mixture was warmed to 45° C. while stirring continuously. Then 0.0009 g (1.26×10⁻⁶ mol) [chlorohydridocarbonylbis(tricyclohexyl-phosphine)ruthenium(II)] was added to the mixture and 5 minutes later 0.0006 g (6.32×10⁻⁶ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:$CH_2Cl_2$=10:1 and transferred to a silica-packed chromatographic column to purify the product. This produced octakis[2-(4-bromophenyl)ethenyl]octasilsesquioxane in the form of white powder with a yield of 88%.

EXAMPLE IX

A 5 mL reactor, equipped with a magnetic stirrer, a reflux condenser with an attachment enabling the reaction system to be connected to a vacuum-and-gas line was filled under inert gas with 0.01 g (1.58×10⁻⁵ mol) octavinylsilsesquioxane, followed, in the following order, with 3 mL toluene and 0.016 mL (1.26×10⁻⁴ mol) 4-bromostyrene. The reaction mixture was warmed to 45° C. while stirring continuously. Then 0.0009 g (1.26×10⁻⁶ mol) [chlorohydridocarbonylbis(tricyclohexylphosphine)ruthenium(II)] was added to the mixture. The reaction mixture was heated for 24 hours at a temperature of 110° C. Then the solvent was subjected to vacuum evaporation and the residue was dissolved in hexane and transferred to a silica-packed chromatographic column to purify the product. This produced octakis[2-(4-bromophenyl)ethenyl]octasilsesquioxane in the form of white powder with a yield of 75%.

EXAMPLE X

A 5 mL reactor, equipped with a magnetic stirrer, a reflux condenser with an attachment enabling the reaction system to be connected to a vacuum-and-gas line was filled under inert gas with 0.01 g (1.58×10⁻⁵ mol) octavinylsilsesquioxane, followed, in the following order, with 3 mL toluene and 0.016 mL (1.26×10⁻⁴ mol) 4-bromostyrene. The reaction mixture was warmed to 45° C. while stirring continuously. Then 0.0012 g (1.26×10⁻⁶ mol) [chlorohydridocarbonyltris(triphenylphosphine)ruthenium(II)] was added to the mixture and 5 minutes later 0.0006 g (6.31×10⁻⁶ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:$CH_2Cl_2$=10:1 and transferred to a silica-packed chromatographic column to purify the product. This produced octakis[2-(4-bromophenyl)ethenyl]octasilsesquioxane in the form of white powder with a yield of 70%.

EXAMPLE XI

A 5 mL reactor, equipped with a magnetic stirrer, a reflux condenser with an attachment enabling the reaction system to be connected to a vacuum-and-gas line was filled under inert gas with 0.01 g (1.58×10⁻⁵ mol) octavinylsilsesquioxane, followed, in the following order, with 3 mL toluene and 0.016 mL (1.26×10⁻⁴ mol) 4-bromostyrene. The reaction mixture was warmed to 110° C. while stirring continuously. Then 0.0009 g (1.26×10⁻⁶ mol) [chlorohydridocarbonylbis(tricyclohexylphosphine)ruthenium(II)] was added to the mixture. The reaction mixture was heated for 24 hours at a temperature of 110° C. Then the solvent was subjected to vacuum evaporation and the residue was dissolved in a mixture of hexane and methylene chloride at a ratio by volume of hexane:$CH_2Cl_2$=10:1 and transferred to a silica-packed chromatographic column to purify the product. This produced octakis[2-(4-bromophenyl)ethenyl]-octasilsesquioxane in the form of white powder with a yield of 52%.

EXAMPLE XII

A 5 mL reactor, equipped with a magnetic stirrer, a reflux condenser with an attachment enabling the reaction system to be connected to a vacuum-and-gas line was filled under inert gas with 0.01 g (1.58×10⁻⁵ mol) octavinylsilsesquioxane, followed, in the following order, with 3 mL methylene chloride and 0.015 mL (1.26×10⁻⁴ mol) 4-chlorostyrene. The reaction mixture was warmed to 45° C. while stirring continuously. Then 0.0009 g (1.26×10⁻⁶ mol) [chlorohydridocarbonylbis(tricyclohexyl-phosphine)ruthenium(II)] was added to the mixture and 5 minutes later 0.0006 g (6.32×10⁻⁶ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:$CH_2Cl_2$=10:1 and transferred to a silica-packed chromatographic column to purify the product. This produced octakis[2-(4-chlorophenyl)ethenyl]octasilsesquioxane in the form of white powder with a yield of 94%. Melting range: 300-302° C.

$^1$H NMR ($C_6D_6$, ppm): δ=6.44 (d, 8H, J=19.0 Hz, =CHSi), 6.97 (s, 32H, $C_6H_4$—Cl), 7.53 (d, 8H, J=19.0 Hz, =CH—Ar)

$^{13}$C NMR ($C_6D_6$, ppm): δ=117.9 (=CHSi), 128.5 (o-C of $C_6H_4$Cl), 129.2 (m-C of $C_6H_4$Cl), 135.5 (ipso-C at Cl of $C_6H_4$Cl), 135.7 (ipso-C of $C_6H_4$Cl), 149.1 (=CHAr)

$^{29}$Si NMR ($C_6D_6$, ppm): δ=−78.06

APPI-MS: m/z ([M+H]⁺, % intensity): 1512 (23), 1513 (26), 1514 (57), 1515 (79), 1516 (92), 1517 (95), 1518 (100), 1520 (80), 1521 (65), 1522 (46), 1523 (32), 1524 (20), 1525 (13)

EXAMPLE XIII

A 5 mL reactor, equipped with a magnetic stirrer, a reflux condenser with an attachment enabling the reaction system to be connected to a vacuum-and-gas line was filled under inert gas with 0.01 g (1.58×10⁻⁵ mol) octavinylsilsesquioxane, followed, in the following order, with 3 mL methylene chloride and 0.023 g (1.26×10$^{-4}$ mol) 4-vinylbiphenyl. The reaction mixture was warmed to 45° C. while stirring continuously. Then 0.0009 g (1.26×10$^{-6}$ mol) [chlorohydridocarbonylbis(tricyclohexyl-phosphine)ruthenium(II)] was added to the mixture and 5 minutes later 0.0006 g (6.32×10$^{-6}$ mol) copper(I) chloride was introduced. The reaction mixture was heated for 24 hours at a temperature of 45° C. Then the solvent was subjected to vacuum evaporation and the residue was dissolved in a mixture of hexane and methylene chloride at a ratio by volume of hexane:CH$_2$Cl$_2$=10:1 and transferred to a silica-packed chromatographic column to purify the product. This produced octakis [2-(4-biphenyl)ethenyl]octasilsesquioxane in the form of white powder with a yield of 83%. Melting range: 280-285° C.

$^1$H NMR (C$_6$D$_6$, ppm): δ=6.75 (d, 8H, J=19.3 Hz, =CHSi), 7.09-7.22 (m, 32H, C$_6$H$_4$—Ph), 7.34-7.46 (m, 40H, =CH—C$_6$H$_4$—C$_6$H$_5$), 7.91 (d, 8H, J=19.3 Hz, =CH—C$_6$H$_4$—Ph)

$^{13}$C NMR (C$_6$D$_6$, ppm):=117.7 (=CHSi), 127.3, 127.4, 128.0, 129.0, 129.1, 136.7, 141.0, 142.3, 150.0 (=CH—C$_6$H$_4$—Ph)

$^{29}$Si NMR (C$_6$D$_6$, ppm): δ=-77.71

APPI-MS: m/z ([M+H]$^+$, % intensity): 1848 (14), 1849 (67), 1850 (100), 1851 (99), 1852 (75), 1853 (49), 1854 (24), 1855 (14), 1856 (9).

Literature:
1. Feher, F. J.; Soulivong, D.; Eklund, A. G.; Wydham, K. D. *Chem. Commun.* 1997, 1185.
2. Itami, Y.; Marciniec, B.; Kubicki, M. *Chem. Eur. J.* 2004, 10, 1239.
3. Sellinger (3) Sellinger, A.; Tamaki, R.; Laine, R. M.; Ueno, K.; Tanabe, H.; Williams, E.; Jabbourd, G. E. *Chem. Commun.* 2005, 3700.

The invention claimed is:
1. Functionalized polyhedral octavinylsilsesquioxanes having the general formula 1, in which:

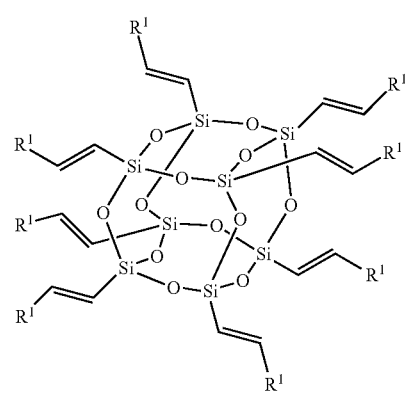

(1)

R$^1$ denotes any heteroaryl group.

* * * * *